US010406192B2

(12) United States Patent
Sorar et al.

(10) Patent No.: US 10,406,192 B2
(45) Date of Patent: Sep. 10, 2019

(54) ARTCURE DIFFUSIONAL PATCH

(71) Applicant: METUAS MEDIKAL SAĞLIK HIZMETLERI DANIŞMANLIK IHRACAT ITHALAT A.Ş. ŞIRKETI, Çankaya-Ankara, Ankara (TR)

(72) Inventors: Mehmet Sorar, Ankara (TR); Tuba Çalik, Ankara (TR)

(73) Assignee: METUAS MEDIKAL SAGLIK HIZMETLERI DANISMANLIK IHRACAT ITHALAT A.S. SIRKETI, Cankaya, Ankara, Ankara (TR)

( * ) Notice: Subject to any disclaimer, the term of this patent is extended or adjusted under 35 U.S.C. 154(b) by 0 days.

(21) Appl. No.: 15/113,209

(22) PCT Filed: Jun. 5, 2014

(86) PCT No.: PCT/TR2014/000194
§ 371 (c)(1),
(2) Date: Jul. 21, 2016

(87) PCT Pub. No.: WO2015/112100
PCT Pub. Date: Jul. 30, 2015

(65) Prior Publication Data
US 2017/0007656 A1    Jan. 12, 2017

(30) Foreign Application Priority Data
Jan. 21, 2014 (TR) ................. 2014 00702

(51) Int. Cl.
| A61K 36/53 | (2006.01) |
| A61K 9/00 | (2006.01) |
| A61K 47/06 | (2006.01) |
| A61K 9/06 | (2006.01) |
| A61K 47/44 | (2017.01) |
| A61K 9/70 | (2006.01) |
| A61K 36/754 | (2006.01) |
| A61K 36/87 | (2006.01) |
| A61K 36/28 | (2006.01) |
| A61K 36/54 | (2006.01) |
| A61K 36/63 | (2006.01) |
| A61K 36/71 | (2006.01) |
| A61K 31/05 | (2006.01) |
| A61K 36/328 | (2006.01) |
| A61K 47/36 | (2006.01) |

(52) U.S. Cl.
CPC ........... *A61K 36/53* (2013.01); *A61K 9/0014* (2013.01); *A61K 9/06* (2013.01); *A61K 9/7023* (2013.01); *A61K 9/7084* (2013.01); *A61K 31/05* (2013.01); *A61K 36/28* (2013.01); *A61K 36/328* (2013.01); *A61K 36/54* (2013.01); *A61K 36/63* (2013.01); *A61K 36/71* (2013.01); *A61K 36/754* (2013.01); *A61K 36/87* (2013.01); *A61K 47/06* (2013.01); *A61K 47/36* (2013.01); *A61K 47/44* (2013.01)

(58) Field of Classification Search
CPC .......... A61K 2039/505; A61K 2039/53; A61K 2039/55566; A61K 39/0216; A61K 2300/00; A61K 36/28; A61K 36/53; A61K 36/54; A61K 36/63; A61K 36/71; A61K 36/754; A61K 36/87; A61K 31/05; A61K 36/328; A61K 47/06; A61K 47/36; A61K 47/44; A61K 9/0014; A61K 9/06; A61K 9/7023; A61K 9/7084
See application file for complete search history.

(56) References Cited

U.S. PATENT DOCUMENTS

| 4,489,711 A * | 12/1984 | Latzke ................ A61F 13/0246 600/15 |
| 2008/0274209 A1* | 11/2008 | Smith .................... A61K 31/05 424/642 |
| 2009/0053290 A1* | 2/2009 | Sand ....................... A61K 8/34 424/449 |

FOREIGN PATENT DOCUMENTS

| TR | 2011/9756 A2 | 6/2012 |
| WO | 2013/074050 A2 | 5/2013 |
| WO | WO2013/074050 A2 * | 5/2013 ............. A61N 2/06 |

OTHER PUBLICATIONS

International Search Report and Written Opinion of the International Searching Authority for corresponding International Patent Application No. PCT/TR2014/000194 dated Oct. 20, 2014, 9 pages.

* cited by examiner

*Primary Examiner* — Audrea B Coniglio
(74) *Attorney, Agent, or Firm* — Merchant & Gould P.C.

(57) ABSTRACT

The present invention is a diffusional patch having an oil mixture (20) providing mechanical treatment support by reducing the edema in volume and in mass by throwing out the liquid inside by means of diffusion effect after entering into the region with edema by means of the diffusion effect and placed into a porous sheath (10) in microfiber structure, in order to be used in treatment of region with edema which may occur in sports injuries and/or disc hernia (50); characterized in that said oil mixture (20), of which the ingredient proportions in weight are given, comprises the below mentioned ingredients and does not comprise water: Ingredient Amount (%) Dextrin Palmitate Derivatives 1-10 Paraffin 1-30 Oleum nigellae sativae (black cumin oil) 0-20 Oleum origani (carvacrol) 0-20 Oleum lauri expressum (laurel oil) 0-30 Oleum chamomillae (chamomile oil) 0-30 Balsamum meccae (balsam oil) 0-30 Styrax liguidus (sweetgum) 0-30 Oleum limonis (lemon oil) 0-10 Oleum rosmarini (rosemary oil) 0-10 Olive oil 0-30 Oleum *vitis vinifera* 0-10.

11 Claims, 2 Drawing Sheets

ARTCURE DIFFUSIONAL PATCH

This application is a National Stage Application of PCT/TR2014/000194, filed 5 Jun. 2014, which claims benefit of Serial No. 2014/00702, filed 21 Jan. 2014, and which applications are incorporated herein by reference. To the extent appropriate, a claim of priority is made to each of the above disclosed applications.

TECHNICAL FIELD

The present invention relates to a diffusional patch used in treatments particularly like disc hernia and sports injuries and edema treatment, and providing mechanical improvement in the related section.

PRIOR ART

Intervertebral disc; is a structure comprising nucleus pulposus and annulus fibrosus and end plates. The extracellular matrix of these structures comprises organic and inorganic compounds having water and collagen, and proteoglycans. The intervertebral discs are avascular tissue elements which are surrounded by extracellular matrix.

Nucleus Pulposus is in the form of viscose liquid, and it is a structure comprising collagen tendons embedded into the gelatinize matrix, and facilitating movement in the lumbar region placed to the ⅓ rear section of the disc. The amount of water of the nucleus pulposus is 88% in young people, however said water amount decreases to 65% in old people. The collagen proportion to the total weight is 20-30%, and besides it comprises proteoglycans like chondroitin sulphate and keratan sulphate, and functional flexibility is provided since liquid continuously displaces therein. Nucleus pulposus is a strong hydrophilic. Since there are no vessels, the feeding thereof is provided by means of diffusion. The colloidal gel is in transaction with the extrinsic liquids and provides liquid balance. By means of the high absorption pressure formed by the gel, it can bind water which is at 9 times the volume thereof. The periphery of the nucleus pulposus is surrounded by annulus fibrosus tendons placed in a concentric manner.

Annulus fibrosus Fibro-elastic collagen has semi-permeable membrane characteristic providing feeding of intervertebral disc by means of diffusional transition. The tendons, wrapping the nucleus pulposus in a tight manner and carrying 75% of the force applied to the disc and forming the structure, are flexible thanks to the arrangement manner of the tendons and thanks to the substantial amount of proteoglycan therein.

Annulus fibrosus histologically comprises collagenous fibrous tissue and fibrous cartilage. The cells thereof have a spectrum from the round chondrocytes to the thin fibroblasts. The tendons of the annulus form concentric layers like onion. The tendons provided in each layer have a slanting movement in a different direction from the adjacent layers which are parallel with respect to each other from one corpus towards the other corpus in an intervertebral interval. Therefore, the bending movements of the backbone are limited by the tensions of the alternative layers. The fibrous bundles occur as a result of the continuation of the tendons existing in the epiphyseal ring at the periphery and the end plate of the cartilage. By means of oblique advancing inside the layer thereof, it draws an arc and enters into the cartilage plate and bone ring provided at the opposite section of the disc. Some of the bundles are mixed with the tendons of the longitudinal spinal ligaments. Some of the bundles turn outwardly and combines with the cortical bone existing on the outer faces of the vertebra corpuses. The water ingredient is lower than nucleus; it is 60-70%. Approximately the 60% of the dry weight is collagen, and approximately 20% of the dry weight is proteoglycans. It also comprises elastic tendons as the minor component (Lumbar Disc Decease, Editor Prof. Dr. Fahri Özer, Logos Publication, October 2000).

If the backbone of a child or a young adult is cut from end to end, the soft jelly substance of the nucleus bulges out towards the cross section surface. The bulging out of the nucleus as a result of cutting or tearing of the sheath wrapping the nucleus can be defined by the term turgescence in the best manner. It is wrong to assess this condition as elasticity. Since, elasticity describes the returning of an object to the original form thereof after said object is extended by means of applying a force thereon. Turgescence can be seen in a very clear manner in a cadaver backbone where the vital stresses like muscle activity, movement and loading are completely eliminated. Therefore, the nucleus in living beings which is under load tries continuously to bulge out from the place where it exists. (Lumbar Disc Decease, Editor Prof. Dr. Fahri Özer, Logos Publication, October 2000).

Under normal conditions, the annulus fibrosus and the cartilage end-plates restraining the nucleus have strength sufficient to prevent bulging out of the nucleus even if it is under big loads. However, there are potentially two weak points in all discs:

1) Cartilage End-Plates,
2) Rear Segment of the Annulus.

The cartilage plate is not supported by a rigid cortical bone; it is supported by the weak spongy bone tissue. The posterior section of the annulus is thinner than the one in the front section and it adheres to the bones in a weaker manner. The disc is herniated from these two points. It is very rare of the nucleus to herniate from the front and lateral sections. (Lumbar Disc Decease, Editor Prof. Dr. Fahri Özer, Logos Publication, October 2000).

The vertebral discs of human beings undergo morphologic and multi-functional biochemical changes in time. The degeneration increasing by age leads to increase in the frequency of lumbar pain and herniated disc. The degenerated discs lead to increase in the amount of pluralities of inflammation mediators which play a role in degenerative processes spontaneously. Studies for explaining the relations of the disease with the degenerative processes are required. Intervertebral discs are non-vascular tissue elements which are surrounded by extracellular matrix.

The annular fibrosus has dominantly collagen structure; however, the center cells thereof are rich in terms of proteoglycans. It is believed that the decrease in proteoglycans as a result of aging is a critical factor in intervertebral disc degeneration. Pluralities of inflammation mediators like nitric oxide (NO), interleukins, prostaglandin E2 (PGE2) and tumor necrosis factor alpha (TNF-alpha) are correlated to intervertebral disc degeneration. In the studies realized, it is observed that most of them play a role in deterioration in the joint cartilage. (Podichetty 2007).

Herniation; is bulging out of the whole or a section of an organ from the normal place thereof, from the sheath or the region thereof. Intervertebral disc herniation is the bulging out of the nucleus pulposus from the annulus fibrosis.

Disc hernia, is the name of the disease occurring as a result of the pathological changes occurring in the shape and ingredient of the discus intervertebralis except the reasons of infection or tumor. Discus intervertebralis are the structures existing between the vertebras and which are responsible for absorption and distribution of the axial loads applied to the column and to the vertebralis. Lumbar disc hernias (LDH) are the most frequently observed disc hernias. Lower lumbar disk hernias form the most important section of the hernias. It is colloquially known as hernia.

Today, pluralities of treatment methods are used in disk hernia disease like conservative treatment, interventional treatment and complementary medicine applications. Even if such methods provide treatment, there is the probability of not presenting an exact solution, and the treatment takes long time and it is difficult. Since the disease continues during the treatment process, the life quality of the patient is low.

The formation of disc hernia, in other words, cervical disc hernia or spinal disc hernia is a mechanical disease. However, after the formation thereof, physio-pathologic process begins. It is evaluated by the medicine world that particularly the oxidative damage plays an effective role in this physio-pathologic process.

In the studies realized in the recent years, it is observed that natural anti-oxidants also comprising the volatile components existing in the plants can prevent oxidative damage and therefore they are protective against inflammatory cell aging (Khanna and others, 2007) and against the neurodegenerative damage processes (Fusco and others).

Terpenoids forming a big section of the chemical ingredients of essential oils penetrate into the cell since they have low molecular weights, and induce different biological activities comprising anti-inflammatory and anti-cholinesterase effects ([Chao and others, 2005], [Kulisic and others, 2007] and [Loizzo and others, 2007]).

The abovementioned section describing the known state of the invention through literatures is particularly related to explanation of the secondary effect for supporting the treatment of disc hernia and for treatment of inflammation in sports injuries and the ache resulting from edema.

In the invention of the applicant with application number 2011/09756, the placement of a mixture, comprising herbal oils, gelling agents and solvents thereof for use in hernia treatment, into a carrier and the effects thereof in hernia treatment are described. Said treatment takes 24 hours on the average. However, some improvements are realized in this new and very effective method.

BRIEF DESCRIPTION OF THE INVENTION

The present invention relates to a diffusional patch improved for eliminating the above mentioned disadvantages of the other treatment methods and for bringing new advantages to the related technical field.

The main object of the present invention is to provide a rapid and mechanical improvement in treatments of disc hernia and sports injuries.

Another object of the present invention is to provide a treatment without surgical intervention.

Another object of the present invention is to provide an improvement which provides treatment without being subject to radiation.

Another object of the present invention is to provide an improvement which realizes treatment of the patient without keeping the patient away from daily facilities.

In order to realize all of the abovementioned objects and the objects which are to be deducted from the detailed description below, the present invention is a diffusional patch having an oil mixture providing mechanical treatment support by reducing the edema in volume and in mass by throwing out the liquid inside by means of diffusion effect after entering into the region with edema by means of the diffusion effect and placed into a porous sheath in microfiber structure, in order to be used in treatment of region with edema which may occur in sports injuries and/or disc hernia. Accordingly, the present invention is characterized in that said oil mixture, of which the ingredient proportions in weight are given, comprises the below mentioned ingredients and does not comprise water:

| Ingredient | Amount (%) |
| --- | --- |
| Dextrin Palmitate Derivatives | 1-10 |
| Paraffin | 1-30 |
| Oleum nigellae sativae (black cumin oil) | 0-20 |
| Oleum origani (carvacrol) | 0-20 |
| Oleum lauri expressum (laurel oil) | 0-30 |
| Oleum chamomillae (chamomile oil) | 0-30 |
| Balsamum meccae (balsam oil) | 0-30 |
| Styrax liguidus (sweetgum) | 0-30 |
| Oleum limonis (lemon oil) | 0-10 |
| Oleum rosmarini (rosemary oil) | 0-10 |
| Olive oil | 0-30 |
| Oleum vitis vinifera | 0-10 |

Thus, since it does not comprise water, the diffusion speed is increased.

In a preferred embodiment of the subject matter invention, said oil mixture comprises ingredients with below mentioned proportions in weight.

| Ingredient | Amount (%) |
| --- | --- |
| Dextrin Palmitate Derivatives | 1-10 |
| Paraffin | 1-30 |
| Oleum nigellae sativae (black cumin oil) | 1-20 |
| Oleum origani (carvacrol) | 1-20 |
| Oleum lauri expressum (laurel oil) | 1-30 |
| Oleum chamomillae (chamomile oil) | 1-30 |
| Balsamum meccae (balsam oil) | 1-30 |
| Styrax liguidus (sweetgum) | 1-30 |
| Oleum limonis (lemon oil) | 1-10 |
| Oleum rossmarini (rosemary oil) | 1-10 |
| Oliva Oleum | 1-30 |
| Oleum vitis vinifera | 1-10 |

In a preferred embodiment of the subject matter invention, said oil mixture penetrates into the hernia approximately in 8 hours after said oil mixture is absorbed by the skin.

In another preferred embodiment of the subject matter invention, said oil mixture decreases the mass of the hernia and decreases the ache within 15-18 hours after said mixture is absorbed by the skin.

In another preferred embodiment of the subject matter invention, said oil mixture decreases the mass of the hernia and decreases the ache within 16 hours after said mixture is absorbed by the skin.

In another preferred embodiment of the subject matter invention, said oil mixture is in semi-solid form.

In another preferred embodiment of the subject matter invention, said oil mixture is in gel form.

In another preferred embodiment of the subject matter invention, said sheath is made of a woven material.

REFERENCE NUMBERS

Figure 1:
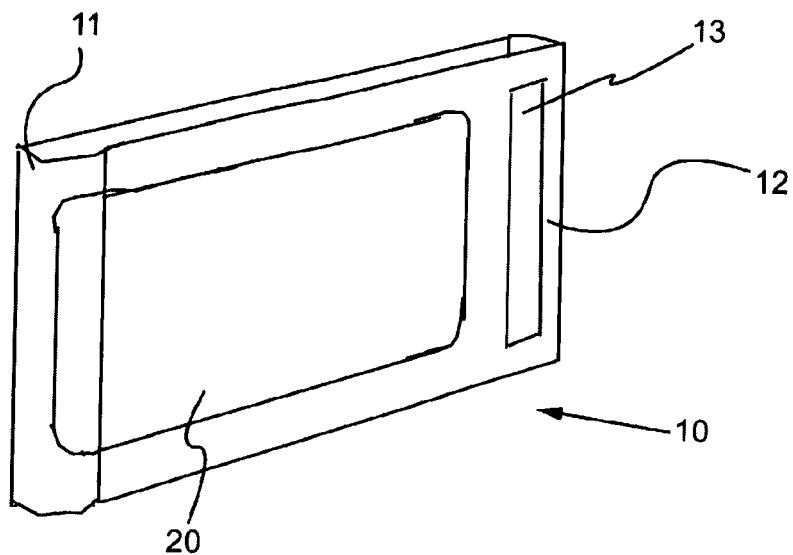
In FIG. 1, a general view of the sheath is given.
Figure 2:
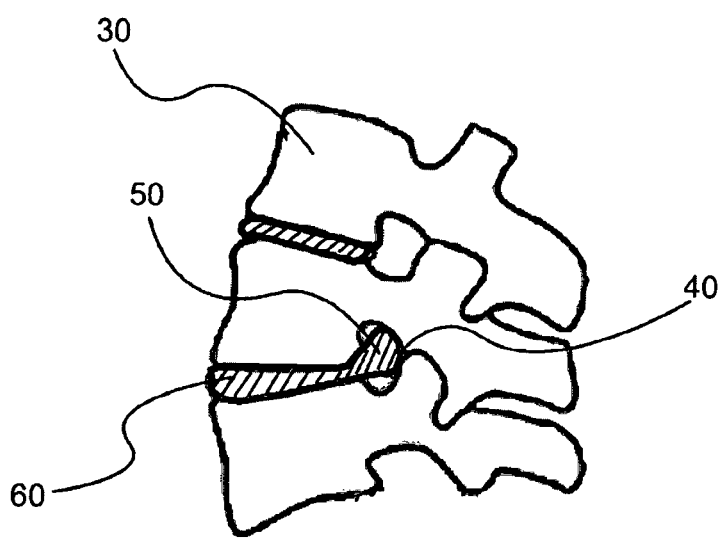
In FIG. 2, a general view of the pressure applied by the hernia on the nerve prior to treatment is given.
Figure 3:
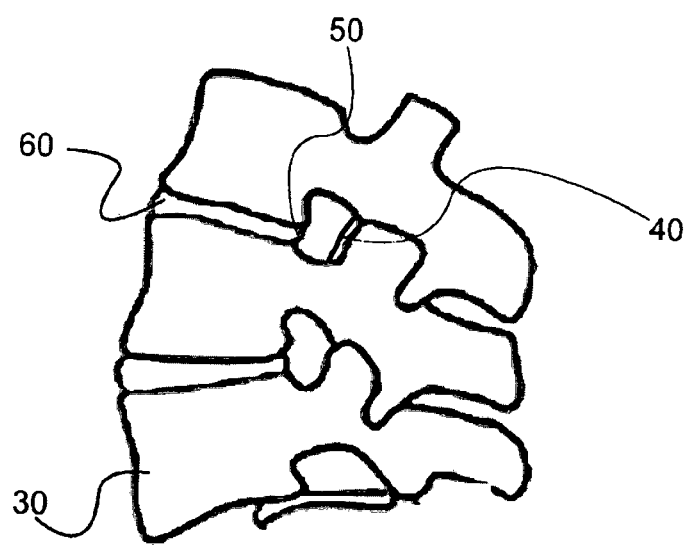
In FIG. 3, a general view of the elimination the pressure on the nerve as a result of diminishing of the hernia after the treatment is given.

10 Sheath
11 Outer section
12 Inner section
13 Band
20 Oil Mixture
30 Vertebra
40 Nerve
50 Hernia
60 Disc structure

THE DETAILED DESCRIPTION OF THE INVENTION

In this detailed description, the subject matter diffusional patch is explained with references to examples without forming any restrictive effect in order to make the subject more understandable.

The diffusional patch generally comprises an oil mixture (20) in gelled form which is placed into a sheath (10) in order to facilitate usage and preservation. The sheath (10) essentially comprises a leak-proof outer section (11), a porous inner section (12), and a band (13) positioned on the outer surface of the inner section (12) for providing holding to the skin. The inner section (12) is made of main medical material with microfiber properties and which may have buffering regions in the bottom and upper regions thereof and whose absorption capacity is high and which is specially woven. The oil mixture (20) is placed between the inner section (12) and the outer section (11), and afterwards, the inner section (11) and the outer section (12) are connected to each other. The interconnection can be realized by means of pluralities of methods like seaming the inner section (12) and the outer section (11) to each other, simmering by means of thermal process, and adhering, etc.

In the oil mixture (20), there are carrier ingredients increasing permeability in the hernia (50) region and accelerating the process. The oil mixture (20) is prepared and placed into the sheath (10) and preserved therein. During usage, the user lifts the bands (13) provided on the sheath (10) and places and adheres the diffusional patch to the region where treatment shall be realized. As the sheath (10) contacts the skin, the oil mixture (20) inside passes through the pores existing on the inner section (12) and it is absorbed by the skin.

The oil mixture (20) is in the form of gel-semi-solid form at room temperature, and when it contacts the skin, it is absorbed by means of the effect of body temperature and the substances of the oil mixture (20) which will show mechanical effect are released. Said oil mixture (20) is a structure in gel form obtained by using at least one gelling agent. In the preferred application, dextrin palmitate derivative is used as the gelling agent. Paraffin is used as the solvent of said dextrin palmitate derivatives. Different components can also be used as the gelling agent.

The oil mixture (20) comprises the ingredients whose ingredient amounts in weight are given below in order to realize the abovementioned objects and the objects which are to be deducted from the detailed description. For the formulation, auxiliary substances can be decreased, increased and supported depending to the regional properties.

| Ingredient | Amount (%) |
| --- | --- |
| Dextrin Palmitate Derivatives | 1-10 |
| Paraffin | 1-30 |
| Oleum nigellae sativae (black cumin oil) | 0-20 |
| Oleum origani (carvacrol) | 0-20 |
| Oleum lauri expressum (laurel oil) | 0-30 |
| Oleum chamomillae (chamomile oil) | 0-30 |
| Balsamium meccae (balsam oil) | 0-30 |
| Styrax liguidus (sweetgum) | 0-30 |
| Oleum limonis (lemon oil) | 0-10 |
| Oleum rossmarini (rosemary oil) | 0-10 |
| Oliva Oleum | 0-30 |
| Oleum Vitis Vinifera | 0-10 |

Hernia (50) is a structure generally formed as a result of bulging out of the disc structure (60), positioned between two vertebras (30), from between said vertebras (30). The disk with hernia as a result of this bulging out applies pressure to the nerve (40) and to the nerve channel. This pressure and the nerve root edema formed as a result of this pressure lead to ache. The surface of the disc structure (60) has a membrane permeable and avascular structure and it is fed by diffusion. Thus, the oils are not absorbed by the disc; they only diffuse into the disc. The disc structure comprises annulus fibrosus which is a rigid membrane surrounding the disc, and nucleus pulposus which is the core section in gel form provided inside said rigid membrane. The inner section of the disc with hernia (50), namely the nucleus pulposus comprises 88% water.

The subject matter diffusional patch is a medical device developed for mitigating the ache occurring due to the hernia (50) in human beings and for supporting treatment of hernia (50). The diffusional patch affects the hernia (50) structure thanks to the diffusional mechanical effect thereof. The diffusional patch is a gelled structure comprising dextrin palmitate derivative as the gelling agent, and comprising formed oil ingredients formulation. The tasks of the formed oils in the formulation are different from each other. Some oils provide the product to be carried to the region where the product is going to provide osmotic balance change, and some formed oil ingredients function as osmotic balance changer. Thus, during the formation of the expected effect, a pharmacologic, immunologic or metabolic reaction is not possible.

In the usage of the diffusional patch in hernia (50) disease; when hernia occurs between the discs, the annulus fibrosus together with the nucleus pulposus becomes excessively herniated (50) or the integrity of the annulus fibrosus may be deteriorated and it may be torn. In both cases, the membrane characteristic of the annulus fibrosus is deteriorated.

The nucleus pulposus, existing inside the hernia (50), has a gel structure and comprises water at proportion of 88%. In the tissue with edema occurring in sports injuries, the liquid density between the cells is increased. The densities of oils are lower than water particularly due to the terpenoids forming a great part of the chemical ingredients. In the present invention, the oils, separating from the gelling agent and from the carrier agent as a result of the body temperature, take charge in different tasks, and move towards the herniated region whose liquid ingredient is more in amount.

The inner density of the nucleus pulposus decreases by means of the input of said oil mixture (10) into the nucleus pulposus. In other words, the nucleus pulposus is mixed with the water therein, and oil+water media is formed which is less dense than water.

The oil mixture (10) realizes the pioneer effect thereof by reaching the hernia region, whose membrane characteristic is deteriorated, thanks to the substances therein increasing permeability. The low density oil mixture (10) passes through the pores of the annulus fibrosus by means of the effect of additional substances increasing permeability and since the membrane characteristic of the annulus fibrosus, which is herniated, is deteriorated; and the oil mixture (10) diffuses in intrinsic distance through the collagenous polar gaps existing on the structure of the nucleus pulposus. Thus, a physically temporary increase occurs in the mass and volume of the herniated disc. This physical mass and volume increase leads to increase of the pressure applied to the nerve root, and may lead to temporary ache increase in the patients in the first 8 hours.

The osmotic pressure of the disc structure whose mass is increased as the oils penetrate into the herniated disc is decreased, and a relative decrease with respect to the peripheral tissues occurs in the density and viscosity of the herniated disc region. The liquid, existing inside the herniated disc (inside the nucleus pulposus) and which is formed into hypo osmos, penetrates into the peripheral tissues, which are relatively more hyper osmos, by means of diffusional effect. Thus, as a result of discharging of the water existing inside the herniated nucleus pulposus, most of the mass and most of the occupied volume are lost, and the pressure applied to the nerve root is eliminated. In other words, the mass weight of the hernia is reduced, and volumetric reduce also occurs in the hernia. At the same time, the clinic symptoms, resulting from the pressure applied by the herniated disc to the nerve root, are also eliminated. Here, the expected result is not the elimination of the herniated disc; the expected result is the clinic improvement formed as a result of elimination of the pressure applied to the nerve. The anti-edema and anti-inflammatory effect resulting from terpenoids existing inside the product can be observed in a secondary manner.

In the animal test realized, it is known that the gel structure shows a strong degeneration in the herniated disc due to the cytotoxic effect of the gel structure. Since the disc is an avascular tissue, and thus since the disc is a tissue which does not renew itself, the degeneration in the herniated disc is irrevocable.

Oleum Limonis and Oleum Rosmarini are used for increasing permeability. The substances like limonene, cineon, pinene existing in these oils function for widening the pores on the skin structure. At the same time, Oleum Lauri Nobilis support permeability. Thus, when the oil mixture (20) is absorbed by the skin and reaches the related hernia (50) region, it can penetrate into the hernia (50) in an easier and more rapid manner.

Oleum chamomilla and Sytrax Liquidus (sweetgum) are volatile oils and they reach first the hernia (50) region thanks to the rapid movement ability and they form a saturated buffer region. As the other oils reach the herniated (50) disc region and reach the region with edema where the liquid between the cells is increased in sports injuries, a volumetrically meaningful region, whose density is lower than the water density, is formed just behind the buffer region.

Oleum *nigellae sativae* (black cumin oil), Oleum chamomillae (chamomile oil), Oleum lauri expressum (laurel oil), Oleum origani (carvacrol), Balsamum meccae (balsam oil), Styrax liguidus (sweetgum) increase the osmotic pressure around the hernia (50) and accelerate diffusion and the penetration amount of the oil mixture (20) into the hernia (50) is also increased.

The main effect of the oil ingredients named Oleum Thymi, Oleum *nigellae sativae* (black cumin oil), Oleum Lauri Nobilis and Oleum Chamomillae, Sytrax Liquidus, Balsamum meccae Oliva oleum is that they decrease the density of the oil mixture thanks to the densities between 0.85-0.92. As the secondary effect, they have anti-edema, anti-inflammatory and anti-oxidant properties.

In experimental studies, it is shown that Oleum *nigellae sativae* (black cumin oil) differentiates the cellular lipid peroxidation of the thymoquinone, existing approximately in proportion of 25%, with the help of eicosanoids, and it forms an anti-inflammatory response, moreover, it can repress the induced arthritis with the help of collagen.

Chamomillae (chamomile) is a plant used in aches of eczema, ulcer, gout, neuralgia and romatoid for many centuries in different cultures. As a result of the studies realized, it is observed that chamomile is a selective COX-inhibitor having anti-inflammatory effects.

Although the researches realized about the gum (Oriental Sweet Gum) obtained from the Styrax liguidus (sweetgum) plant epidemically growing in Turkey are limited, it is considered that it has anti-inflammatory, antiseptic and antibacterial effects thanks to the resins thereof.

In summary, the oil mixture (10), developed in the subject matter invention, penetrates into the hernia (50) by means of diffusion, and discharges the water therein outwardly, and afterwards it is absorbed and discharged from the body. Thus, the hernia (50) is deflated, and the connection thereof to the nerve, pressure is applied thereto, is broken, and the ache is eliminated. The duration of elimination of the ache after application of the oil mixture is 16 hours on the average. After 24 hours on the average, the oil mixture is discharged from the body.

In this product, developed as a result of the studies realized at the continuation of the invention with number 2011/09756, the liquid ingredient, which is among the ingredients in said invention, is decreased and even completely eliminated. Thus, the oil mixture (20) is reduced to certain number of ingredients, and the same effect is obtained in a much more rapid manner. Since water is removed from the oil mixture (20), the osmotic pressure effect of the periphery of the hernia (50) is increased, and penetration of the oil mixture (20) into the hernia and the discharge of water from the hernia (50) are accelerated. Thus, the treatment duration is also shortened. Besides, the chemical ingredients like cetyl alcohol, stearyl alcohol used as solvent, sodium lauryl sulfate used for making the mixture like a cream; liquid vaseline used for occupying volume and for increasing absorption; lanoline used for increasing absorption, are removed from the oil mixture (20), and as a result of this, the skin is less irritated and at the same time, the skin is in contact with less number of chemical substances.

In the preferred application, the mixture proportions used are as follows.

| Ingredient | Amount (%) |
| --- | --- |
| Dextrin Palmitate Derivatives | 1-10 |
| Paraffin | 1-30 |
| Oleum nigellae sativae (black cumin oil) | 1-20 |
| Oleum origani (carvacrol) | 1-20 |
| Oleum lauri expressum (laurel oil) | 1-30 |
| Oleum chamomillae (chamomile oil) | 1-30 |
| Balsamum meccae (balsam oil) | 1-30 |
| Styrax liguidus (sweetgum) | 1-30 |
| Oleum limonis (lemon oil) | 1-10 |
| Oleum rossmarini (rosemary oil) | 1-10 |
| Oliva Oleum | 1-30 |
| Oleum vitis vinifera | 1-10 |

In an alternative embodiment of the present invention, a magnetic material is used placed to the right and left side of the microfiber sheath (10) and which can be formed by interspersing magnetic units into the oil mixture (20) in solid-semi-solid form depending of the application manner or which can also be designed so as to be used externally together with the application. Thus, the present invention also forms a magnetic effect. The magnetic effect is known to be used for treatment of arthrolith in 3$^{rd}$ century before common-era in the form of magnetized metals, and for the treatment of gout disease, hairlessness and poisoning treatment in the middle-ages by doctors. Today, as in the old times, in pluralities of treatments, the metals/magnets where static electricity is loaded are used as auxiliary to the treatments since these metals/magnets have a capacity to form a continuous power flow.

Even if there are no sufficient clinical studies about this, it is mentioned that the magnets regulate blood flow, they increase the amount of oxygen in the body, they increase lymph drainage, and they relax the muscles. Magnets have a positive effect on people for treatment.

In another alternative embodiment of the present invention, Oleum *vitis viniferae* (grape seed oil) is added to the oil mixture (20) for utilizing the antioxidant effect of the grape seed oil.

In the present invention, the herbal oil ingredients are given with the names mentioned in Pharmacopeia. No information about the origin thereof is given. The main effect and mechanism of the present invention is based on the displacement of water formed as a result of the diffusion effect; and it is considered that the antioxidant and anti-edema effect will provide support to the condition formed after the physio-pathologic process.

The protection scope of the present invention is set forth in the annexed Claims and cannot be restricted to the illustrative disclosures given above, under the detailed description. It is because a person skilled in the relevant art can obviously produce similar embodiments under the light of the foregoing disclosures, without departing from the main principles of the present invention.

The invention claimed is:

1. A diffusional patch for reducing edema of a herniated disc comprising a volume of water, the diffusional patch comprising a microfiber porous sheath and an anhydrous oil mixture, the anhydrous oil mixture being contained within the microfiber porous sheath, the diffusional patch comprising no water, and the anhydrous oil mixture comprising the following ingredients in the listed weight ranges:

| Ingredient | Amount (%) |
|---|---|
| Dextrin Palmitate based gelling agent | 1-10 |
| Paraffin | 1-30 |
| Oleum nigellae sativae | 1-20 |
| Oleum origani | 1-20 |
| Oleum lauri expressum | 1-30 |
| Oleum chamomillae | 1-30 |
| Balsamum meccae | 1-30 |
| Styrax liguidus | 1-30 |
| Oleum limonis | 1-10 |
| Oleum rossmarini | 1-10 |
| Olive oil | 1-30 |
| Oleum vitis vinifera | 1-10 | wherein, the anhydrous oil mixture is configured to exit the porous microfiber sheath and diffusably penetrate into the herniated disc to cause the herniated disc to discharge the volume of water from the herniated disc.

2. A diffusional patch according to claim 1, wherein said oil mixture penetrates into the hernia approximately in 8 hours after said oil mixture is absorbed by the skin.

3. A diffusional patch according to claim 1, wherein said oil mixture decreases the mass of the hernia and decreases the ache within 15-18 hours after said mixture is absorbed by the skin.

4. A diffusional patch according to claim 3, wherein said oil mixture decreases the mass of the hernia and decreases the ache within 16 hours after said mixture is absorbed by the skin.

5. A diffusional patch according to claim 1, wherein said oil mixture is in semi-solid form at room temperature.

6. A diffusional patch according to claim 1, wherein said oil mixture is in gel form at room temperature.

7. A diffusional patch according to claim 1, wherein said sheath is made of a woven material.

8. A diffusional patch according to claim 1, comprising magnetic material provided on said sheath.

9. A diffusional patch according to claim 8, wherein the magnetic material is formed by interspersing magnetic units into said anhydrous oil mixture.

10. A diffusional patch according to claim 1, wherein said sheath comprises a leak-proof outer section.

11. A diffusional patch according to claim 1, wherein said sheath comprises a porous inner section having buffering regions.

* * * * *